United States Patent
Rump et al.

(10) Patent No.: US 9,289,602 B2
(45) Date of Patent: Mar. 22, 2016

(54) ELECTRODE LINE OR ELECTRODE PORTION OF AN ELECTRODE LINE

(71) Applicant: BIOTRONIK SE & CO. KG, Berlin (DE)

(72) Inventors: Jens Rump, Berlin (DE); Heinrich Buessing, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/463,501

(22) Filed: Aug. 19, 2014

(65) Prior Publication Data

US 2015/0057732 A1  Feb. 26, 2015

Related U.S. Application Data

(60) Provisional application No. 61/869,767, filed on Aug. 26, 2013.

(51) Int. Cl.
*A61N 1/05* (2006.01)
*H01B 3/12* (2006.01)

(52) U.S. Cl.
CPC .............. *A61N 1/0565* (2013.01); *A61N 1/05* (2013.01); *H01B 3/12* (2013.01)

(58) Field of Classification Search
CPC ................................ A61N 1/0472; A61N 1/05
See application file for complete search history.

(56) References Cited

U.S. PATENT DOCUMENTS

| | | | |
|---|---|---|---|
| 8,165,697 B2 | 4/2012 | Rodriguez et al. | |
| 2005/0084672 A1 | 4/2005 | O'Brien | |
| 2008/0177353 A1 | 7/2008 | Hirota et al. | |
| 2010/0305671 A1 * | 12/2010 | Specht et al. | 607/115 |

FOREIGN PATENT DOCUMENTS

| | | |
|---|---|---|
| EP | 0787507 A1 | 9/2003 |
| EP | 1574181 A1 | 9/2005 |

OTHER PUBLICATIONS

European Search Report received from EP Application Serial No. 14174639, dated Nov. 27, 2014, 5 pages.

* cited by examiner

*Primary Examiner* — Eric D. Bertram
(74) *Attorney, Agent, or Firm* — Arc IP Law, PC; Joseph J. Mayo

(57) ABSTRACT

An elongate implantable electrical line including an end component at one longitudinal end of the electrical line, wherein the end component includes at least one electrically conductive electrode surface electrically connected to the electrical line. The end component is a composite component that includes at least one thin metal layer with a layer thickness less than 1 µm. The at least one thin metal layer is applied to electrically insulating material of the composite component and is conductively connected to the electrical line, such that the at least one thin metal layer includes, or acts as, an electrode surface. The at least one thin metal layer includes an outer surface and is completely covered completely by at least one outer ceramic layer on the outer surface, such that the at least one thin metal layer is electrically insulated from a surrounding environment.

14 Claims, 3 Drawing Sheets

ELECTRODE LINE OR ELECTRODE PORTION OF AN ELECTRODE LINE

This application claims the benefit of U.S. Provisional Patent Application 61/869,767, filed on 26 Aug. 2013, the specification of which is hereby incorporated herein by reference.

BACKGROUND OF THE INVENTION

1. Field of the Invention

Embodiments of the invention generally relate to an elongate implantable electrical line including an end component at one longitudinal end of the electrical line, wherein the end component includes at least one electrically conductive electrode surface electrically connected to the electrical line.

2. Description of the Related Art

Generally, elongate implantable electrical lines typically include electrode lines such as stimulation electrode lines for implantable cardiac pacemakers or defibrillators. Such electrode lines, typically, include a proximal end with an electrical terminal for connection of the electrode line to a stimulation device, such as a cardiac pacemaker or defibrillator, and also a distal end with stimulation or sensing electrodes. Generally, an electrode head is often arranged at the distal end of an electrode line and forms a tip electrode. Typically, one or more ring electrodes may also be provided at a short distance from the tip electrode.

European Patent 0787507 to Ekwall, entitled "Medical Device Used to Stimulate Tissue", appears to disclose a stimulation electrode line, wherein a metal electrode is completely coated with an insulating layer. The device of Ekwall uses, for example, titanium as the metal of the electrode, and titanium oxide as the insulating layer on the electrode with a layer thickness of 1 µm. According to Ekwall, aluminum may be used as the metal of the electrode and aluminum oxide as the material of the insulating layer.

Ceramic layers have also been utilized with electrodes. Generally, ceramic layers have the disadvantage of having small holes or imperfections, also referred to as pinholes, which may cause a metal layer of an electrode line to no longer be galvanically isolated from the environment surrounding a composite component of the electrode line.

Typically, an outer ceramic layer is mechanically and chemically stable, even at low thickness, however ceramic layers are typically sensitive to electrical effects, such as spark erosion. Generally, small imperfections in the coating (such as the pinholes) lead to formation of plasma channels in the event of an electrical load. Generally, the plasma channels, in the event of an electrical discharge, generate temperature peaks that lead to damage of both an insulating layer and a support layer. Typically, any damage of this type may lead to malfunction of the electrode in the event of sensing or stimulation (such as pacing). Generally, a mere increase of the layer thickness of the ceramic layer does not increase the long-term stability thereof since pinholes typically cannot be closed or avoided by increasing the layer thickness.

In view of the above, there is a need for an electrode line with a composite component, a thin metal layer and a ceramic layer, such that, in the event of a pinhole, the thin metal layer not located in the region of the pinhole is electrically insulated from the environment surrounding the composite component.

BRIEF SUMMARY OF THE INVENTION

One or more embodiments of the invention are related to an elongate electrical line with an end component and a method of producing an elongate electrical line.

In at least one embodiment, the end component may be a composite component with at least one thin metal layer with a layer thickness less than 1 µm for example. In one or more embodiments, the thin metal layer may be applied to electrically insulating material of the composite component. In at least one embodiment, the at least one thin metal layer may be conductively connected to the electrical line and may include, or act as, an electrode surface. According to one or more embodiments, an outer face of the at least one thin metal layer may be completely or substantially completely covered by at least one outer ceramic layer. In at least one embodiment, the at least one thin metal layer may be completely covered by the outer ceramic layer and may be electrically insulated from the surrounding environment. The inventors have recognized disadvantages that accompany the basic advantages of ceramic insulating layers and in one or more embodiments of the invention provide a thin metal layer the composite component, such that, in the event of an imperfection such as a pinhole, the thin metal layer vaporizes as a result of an applied electrical discharge, wherein the outer ceramic layer is removed by spark erosion in a region of the imperfection or pinhole. As such, in one or more embodiments, the rest of the thin metal layer not located in the region of the pinhole is completely electrically insulated from the environment surrounding the composite component.

Suitable layer thicknesses for the at least one outer ceramic layer, in at least one embodiment, may be smaller than 10 µm and greater than 1 µm. In one or more embodiments, the at least one thin metal layer may have a layer thickness of less than 100 nm, such as 10 nm.

According to at least one embodiment, the electrically insulating material to which the thin metal layer is applied may include a ceramic material. In at least one embodiment, the electrically insulating material may be an insulating layer that is applied to a metal main body. By way of one or more embodiments, the insulating layer may include a ceramic material and may have imperfections, such as pinholes, similar to the imperfections in the at least one outer ceramic layer, such that the at least one thin metal layer may electrically contact the metal main body. In at least one embodiment, a pinhole in the insulating layer beneath the at least one thin metal layer may not be located at the same point as a pinhole in the at least one outer ceramic layer. In one or more embodiments, a pinhole in the electrically insulating material layer and to which the at least one thin metal layer is applied to may be eliminated. In at least one embodiment, to increase a level of security, a plurality of insulating layers and plurality of thin metal layers may be arranged one after the other, in an alternating manner, such that the composite component includes a plurality of thin metal layers and insulating layers arranged therebetween, wherein these insulating layers may include ceramic layers. In at least one embodiment, the at least one metal layer may be thinner than the corresponding ceramic layers.

According to one or more embodiments, materials for the at least one ceramic layer may include one or more of silicon oxide, silicon carbide, and a metal oxide, such as aluminum oxide or tantalum oxide. In at least one embodiment, the at least one thin metal layer may be a titanium layer. In one or more embodiments, a material of the metal main body, which may or may not be provided, may include titanium.

By way of at least one embodiment, the at least one thin metal layer, or an outermost thin metal layer of the plurality of thin metal layers, may include or act as an electrode surface, and the elongate electrical line may include, or act as, a stimulation electrode line, such as an electrode line of an implantable stimulation device, a cardiac pacemaker or a defibrillator.

In one or more embodiments, the composite component of the elongate electrical line may be produced or provided independently of the rest of the elongate electrical line as a separate component.

In at least one embodiment, the electrical line and in particular its composite component may be generated using a production method in which the one or more ceramic layers may be applied to the composite component using physical vapor deposition (PVD). In one or more embodiments, the production method may also including applying one or more thin metal layers to the electrically insulating material using chemical vapor deposition (CVD).

One or more embodiments of the invention may include applying an electrical discharge, such as an electrical voltage, to produce spark erosion in order to vaporize the at least one thin metal layer in the region of pinholes in the outer ceramic layer. This step may occur during use or during production of the electrical line according to at least one embodiment the invention or of the composite component according to at least one embodiment the invention.

By way of at least one embodiment, the composite component may include an electrode head for a stimulation electrode line.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
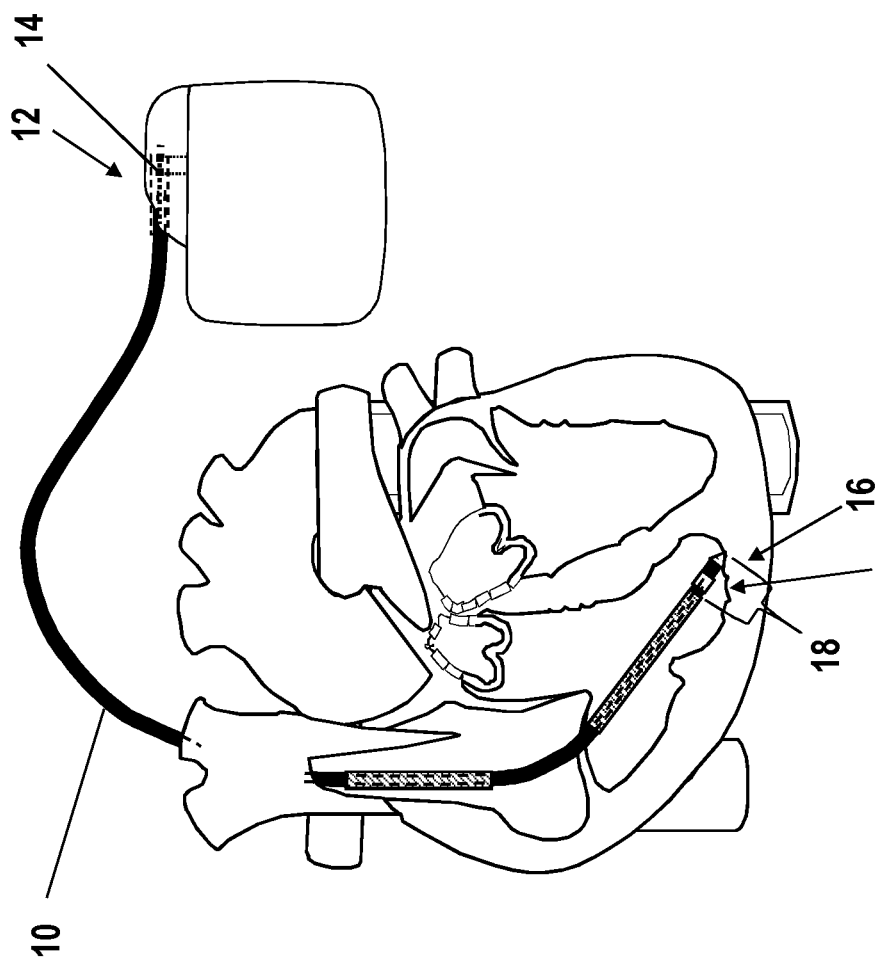
FIG. 1: shows a schematic view of a stimulation electrode line according to at least one embodiment of the invention.

FIG. 1 shows a schematic view of a stimulation electrode line according to at least one embodiment of the invention. As shown in FIG. 1, one or more embodiments of the invention include an electrode line 10 having a proximal end 12 with an electrical plug connection 14. In at least one embodiment, the electrode line 10 includes a distal end 16 with an electrode head 18, wherein the electrode head 18 may be a composite component. By way of at least one embodiment, the electrode line 10 is an elongate electrical line and may include at least one electrical conductor that extends from the proximal end to the distal end and produces an electrical connection between the electrode head 18 (or the composite component) and the electrical terminal 14. In one or more embodiments, the at least one electrical conductor may include titanium. In at least one embodiment, the electrode head 18 (or the composite component) may include a main body made of titanium. In one or more embodiments, the electrode line 10 may be transparent to an X-ray.

Figure 2:
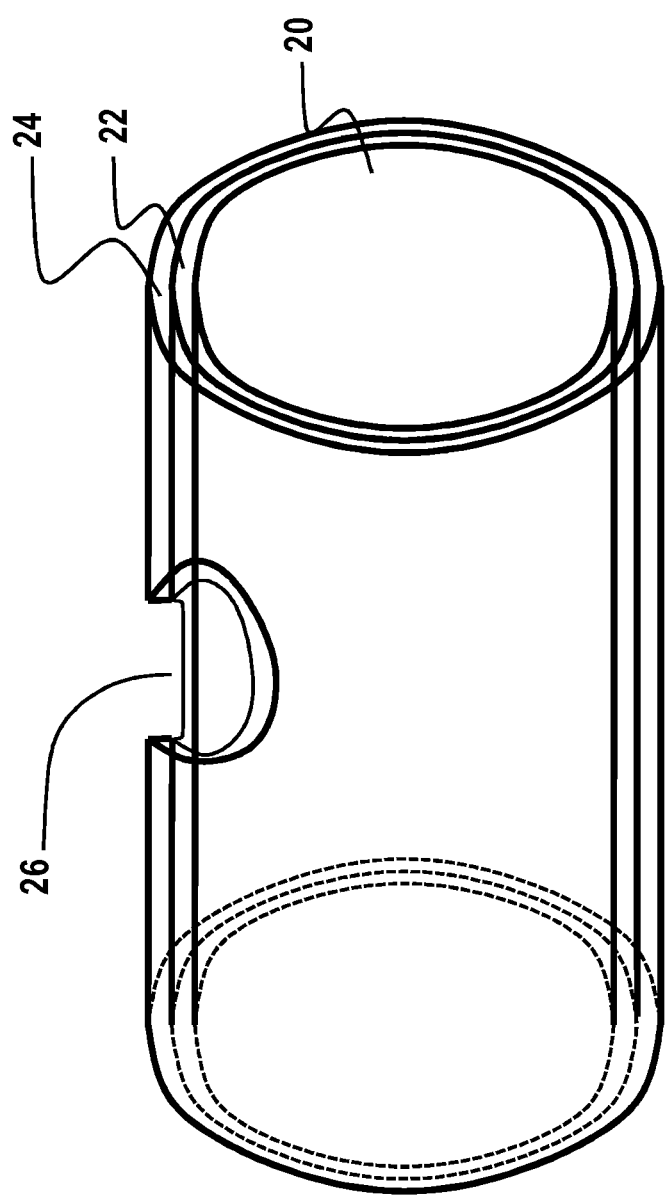
FIG. 2: shows a schematic illustration of a composite component having a main body formed from electrically non-conductive material, a thin metal layer and an outer ceramic layer, according to at least one embodiment of the invention.
Figure 3:
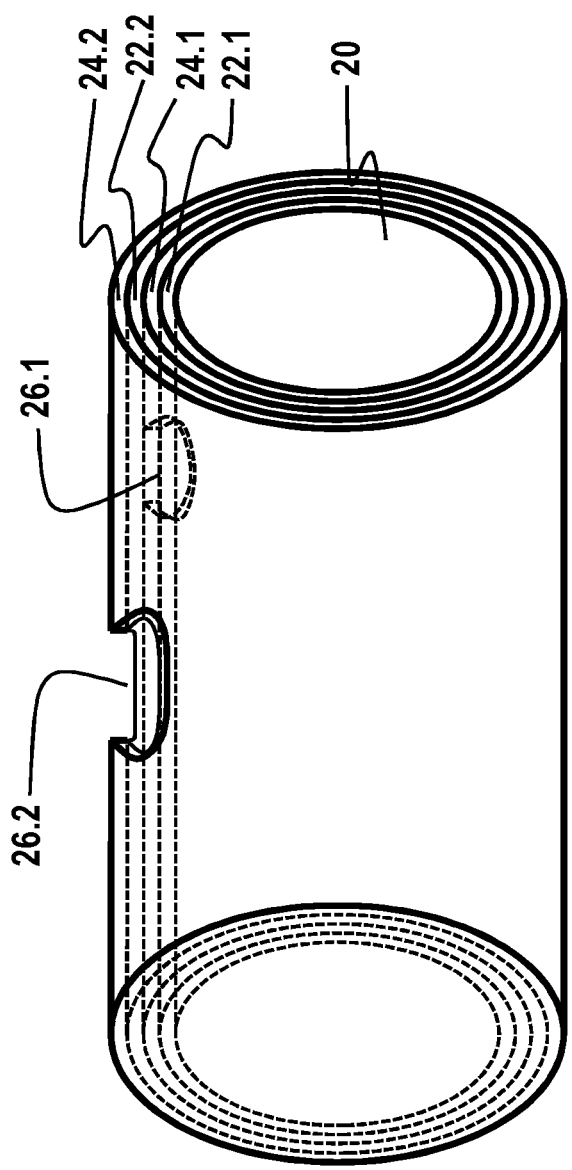
FIG. 3: shows a schematic illustration of a composite component having a plurality of metal layers and a plurality of ceramic layers, according to at least one embodiment of the invention.

FIGS. 2 and 3 show schematic illustrations of the electrode head as a composite component according to at least one embodiment of the invention. In one or more embodiments, at least one metal layer 22 may be applied to an insulating main body 20. In at least one embodiment, the metal layer may be covered completely, or substantially completely, on an outer face, by a ceramic layer 24 such as an insulating layer.

By way of at least one embodiment, the electrically insulating main body 20 may include of a plurality of components and may include a metal main body to which an inner insulating layer, such as a ceramic layer, may be applied. One or more embodiments may include an insulating layer located between the main body 20 (as illustrated in FIG. 2) and the metal layer 22.

FIG. 2 shows a schematic illustration of a composite component having a main body formed from electrically non-conductive material, a thin metal layer and an outer ceramic layer, according to at least one embodiment of the invention. As shown in FIG. 2, one or more embodiments include the outer ceramic layer 24 that may include an imperfection 26, such that the metal layer 22 in the region of the imperfection 26 may not be galvanically isolated, by the outer ceramic layer 24, from the environment surrounding the composite component of electrode head 18. As such, in at least one embodiment, spark erosion may occur in the region of the imperfection 26, leading to the vaporization of the metal layer 22 in the region of the imperfection 26, such that the remaining metal layer 22 is galvanically isolated from the environment surrounding the composite component of electrode head 18.

FIG. 3 shows a schematic illustration of another embodiment of composite component of electrode head 18 similar to the composite component of electrode head 18 discussed above regarding FIG. 2, including a plurality of metal layers and a plurality of ceramic layers. One or more embodiments of the invention include an additional imperfection 26.1 in an insulating layer 24.1 arranged between two metal layers 22.1 and 22.2 that is insignificant, however imperfection 26.1 may be eliminated since it is covered by a second metal layer 22.2 and the outer ceramic layer 24.2. At least one embodiment of the invention may include imperfection 26.2, identical to the imperfection 26 discussed above regarding FIG. 2. In one or more embodiments, by applying an electrical voltage, spark erosion may occur in the region of the imperfection 26.2 and, as a result, the metal layer 22.2 vaporizes in the region of the imperfection 26.2.

According to at least one embodiment, insulation at head electrodes or sleeves on implantable electrodes may be eroded by chemical, electrical and/or mechanical external influences. In one or more embodiments, with a sandwich design of alternate one or more thin metal and ceramic layers, the mechanical strength of the insulation is ensured by the one or more ceramic layers. In at least one embodiment, imperfections in the at least one ceramic layer may be treated by the application of the electrical voltage (discharge) to the one or more thin metal layers using spark erosion, and as such the long-term stability of the device may be increased. One or more embodiments of the invention include an insulating thin layer (of <10 μm), which may be resistant to one or more of a mechanical, chemical and electrical load, and may be chemically inert and stable with respect to mechanical and electrical influences. As such, in at least one embodiment, the insulating thin layer may enable long-lasting stability of electrical properties, such as direct current (DC) resistance, of the coating, and prevents undesired erosion.

In one or more embodiments, to produce, for an implantable electrode line, a titanium head electrode or sleeve that is transparent to X-ray, a silicon carbide (SiC) of 1-2 μm thick may be applied, using PVD methods to a main body made of titanium. By subsequent coating with titanium, in at least one embodiment, the SiC layer may be metallized until a titanium layer of a few nanometers thick (<500 nm) is produced. In one or more embodiments, pinholes may be filled by the metal, such as titanium, and the at least one thin metal layer may be electrically connected to the main body made of titanium. In at least one embodiment, a second SiC layer may be applied over the at least one thin metal layer by sputtering. It is very unlikely that pinholes produced during this process will be located above the pinholes in the lower SiC layer. The likelihood can be further reduced by, in one or more embodiments, increasing the number of layers to three or more layers.

In at least one embodiment, an electrical voltage may be applied to the composite component, such that spark erosion is produced at the pinholes in the outer SiC layer and the thin metallization located at or about the pinholes is vaporized.

In one or more embodiments, the outer pinhole and inner head sleeve may be electrically separated from one another after the spark erosion, wherein self-healing is thus produced.

As shown in FIG. 3, compared to FIG. 2, the composite component includes a plurality of metal layers and a plurality of insulating layers. By way of at least one embodiment, the outer ceramic layer 24 of the electrode line may be damaged by a mechanical, chemical or electrical load (such as imperfection 26) during the course of the use of the electrode line, the underlying outer metal layer 22 is galvanically connected to the environment surrounding the composite component (for example an electrolyte such as blood) and the function of the electrode is impaired.

As such, in at least one embodiment, the composite component may include a plurality of metal layers 22.1 and 22.2 and ceramic layers 24.1 and 24.2, such that an imperfection 26.2 in the outer ceramic layer 26.2 may result in the inner metal layer 22.1 being protected by the middle ceramic layer 24.1 and the outer metal layer 22.2, before the infiltration of the electrolyte, such as blood, and before further break-up.

One or more embodiments of the invention enable high strength of a thin insulation of electrodes of less than 10 μm for example as well as high manufacturing tolerance. By way of at least one embodiment, imperfections that may be located in the ceramic layer, and which may impair the functionality of the electrode, may be subsequently electrically treated.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An elongate implantable electrical line comprising:
    an end component at a first longitudinal end of the elongate implantable electrical line, wherein the end component comprises
        at least one electrically conductive electrode surface electrically connected to the elongate implantable electrical line, and,
        a composite component that comprises
            an electrically insulating main body comprising
                a metal main body and,
                an inner insulating layer applied to the metal main body;
            at least one outer ceramic layer;
            at least one thin metal layer with an outer surface, and a layer thickness of less than 1 μm, which is coupled to the electrically insulating main body;
            wherein the at least one thin metal layer is conductively connected to the electrical line;
            wherein the at least one thin metal layer is applied to the electrically insulating main body; and,
            wherein the at least one thin metal layer is covered on said outer surface by the at least one outer ceramic layer, such that said at least one thin metal layer is between said electrically insulating main body and said at least one outer ceramic layer, wherein the at least one thin metal layer forms the at least one electrically conductive electrode surface, and wherein the at least one thin metal layer is electrically insulated by the at least one outer ceramic layer such that the at least one thin metal layer is configured to be electrically insulated from an environment surrounding the composite component.

2. The elongate implantable electrical line as claimed in claim 1, wherein said at least one outer ceramic layer comprises an imperfection or a pinhole, and wherein the at least one thin metal layer vaporizes as a result of an applied electrical discharge in a region of the imperfection or pinhole, wherein the at least one outer ceramic layer is removed by spark erosion in the region of the imperfection or pinhole, and wherein a remaining portion of the at least one thin metal layer not located in the region of the imperfection or pinhole is completely electrically insulated from an environment that surrounds the composite component by said at least one outer ceramic layer not located in the region of the imperfection or pinhole.

3. The elongate implantable electrical line as claimed in claim 1, wherein the at least one outer ceramic layer comprises a layer thickness of less than 10 μm.

4. The elongate implantable electrical line as claimed in claim 1, wherein the at least one outer ceramic layer comprises a layer thickness of greater than 1 μm.

5. The elongate implantable electrical line as claimed in claim 1, wherein the at least one thin metal layer comprises a layer thickness of less than 100 nm.

6. The elongate implantable electrical line as claimed in claim 1, wherein the inner insulating layer comprises a ceramic material.

7. The elongate implantable electrical line as claimed in claim 1, wherein the composite component further comprises a plurality of thin metal layers and a plurality insulating layers arranged in an alternating manner, wherein the plurality of insulating layers are arranged between the plurality of thin metal layers.

8. The elongate implantable electrical line as claimed in claim 7, wherein at least one of the plurality of insulating layers comprises a ceramic layer.

9. The elongate implantable electrical line as claimed in claim 1, wherein the inner insulating layer comprises a ceramic layer.

10. The elongate implantable electrical line according to claim 1, wherein the at least one thin metal layer is thinner than the at least one outer ceramic layer.

11. The elongate implantable electrical line as claimed in claim 1, wherein the at least one outer ceramic layer comprises one or more of silicon oxide, silicon carbide, and a metal oxide, wherein the metal oxide comprises one or more of an aluminum oxide and a tantalum oxide.

12. The elongate implantable electrical line as claimed in claim 1, wherein the at least one thin metal layer, the electrically insulating main body and the at least one outer ceramic layer together comprise a thickness of less than 10 µm.

13. The elongate implantable electrical line as claimed in claim 1, further comprising a stimulation electrode line comprising the first longitudinal end.

14. A method for producing an electrical line as claimed in claim 1, wherein the at least one ceramic layer is applied using physical vapor deposition (PVD) or chemical vapor deposition (CVD).

\* \* \* \* \*